United States Patent [19]

Morrow et al.

[11] Patent Number: 4,790,824

[45] Date of Patent: Dec. 13, 1988

[54] NON-INVASIVE HYPODERMIC INJECTION DEVICE

[75] Inventors: J. Thomas Morrow, Beaverton, Oreg.; Marvin Burns, Marina Del Rey, Calif.

[73] Assignee: Bioject, Inc., Portland, Oreg.

[21] Appl. No.: 64,762

[22] Filed: Jun. 19, 1987

[51] Int. Cl.⁴ ............................................. A61M 37/00
[52] U.S. Cl. ................................................... 604/143
[58] Field of Search .................. 604/68, 70, 71, 72, 604/140, 141, 143, 187, 131

[56]  References Cited

U.S. PATENT DOCUMENTS

| | | |
|---|---|---|
| 2,547,099 | 4/1951 | Smoot . |
| 2,704,543 | 3/1955 | Scherer . |
| 2,737,946 | 3/1956 | Hein, Jr. . |
| 2,764,977 | 10/1956 | Ferguson . |
| 3,688,765 | 9/1972 | Gasaway . |
| 3,695,266 | 10/1972 | Lussier . |
| 3,853,125 | 12/1974 | Clark et al. . |
| 3,945,379 | 3/1976 | Pritz et al. . |
| 3,945,383 | 3/1976 | Bennett et al. . |
| 4,403,989 | 9/1983 | Christensen et al. . |
| 4,596,556 | 6/1986 | Morrow et al. . |
| 4,680,027 | 7/1987 | Parsons et al. ................. 604/68 |

FOREIGN PATENT DOCUMENTS 492587  5/1953  Canada .

Primary Examiner—John D. Yasko
Attorney, Agent, or Firm—Kolisch, Hartwell & Dickenson

[57] ABSTRACT

A non-invasive hypodermic injection device includes a two-stage gas delivery system and a medication containing ampule having a truncated hypodermic needle at one end thereof. An ampule shroud encloses the ampule and maintains separation between the truncated hypodermic needle on the ampule and the skin of a patient being injected.

24 Claims, 2 Drawing Sheets

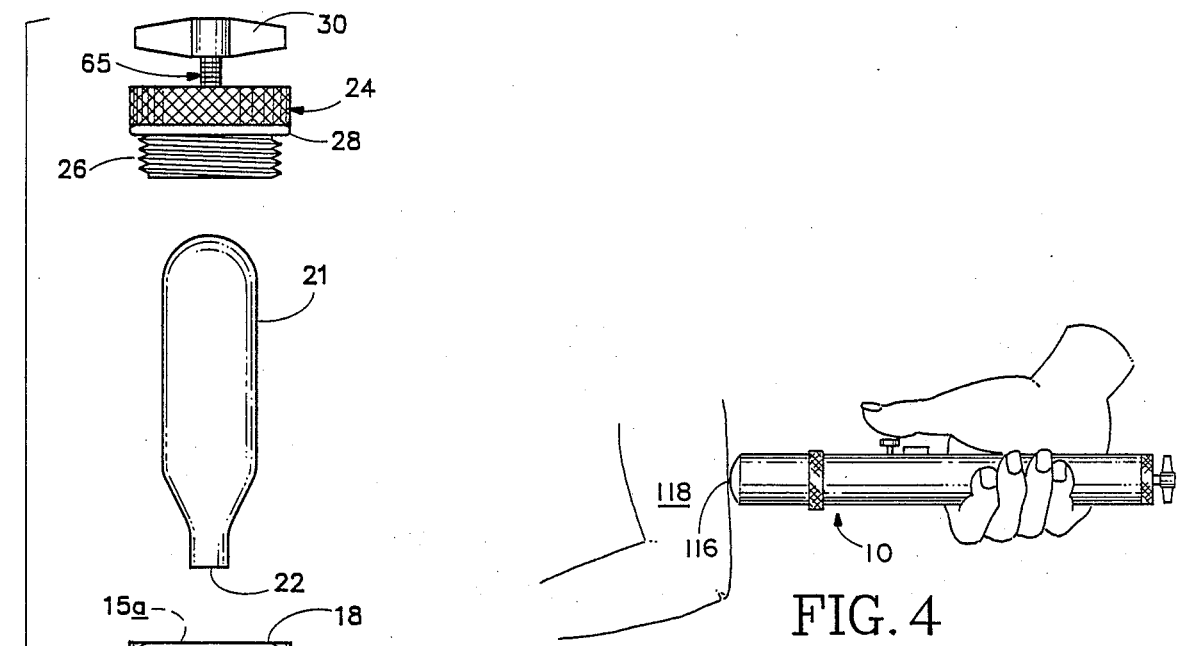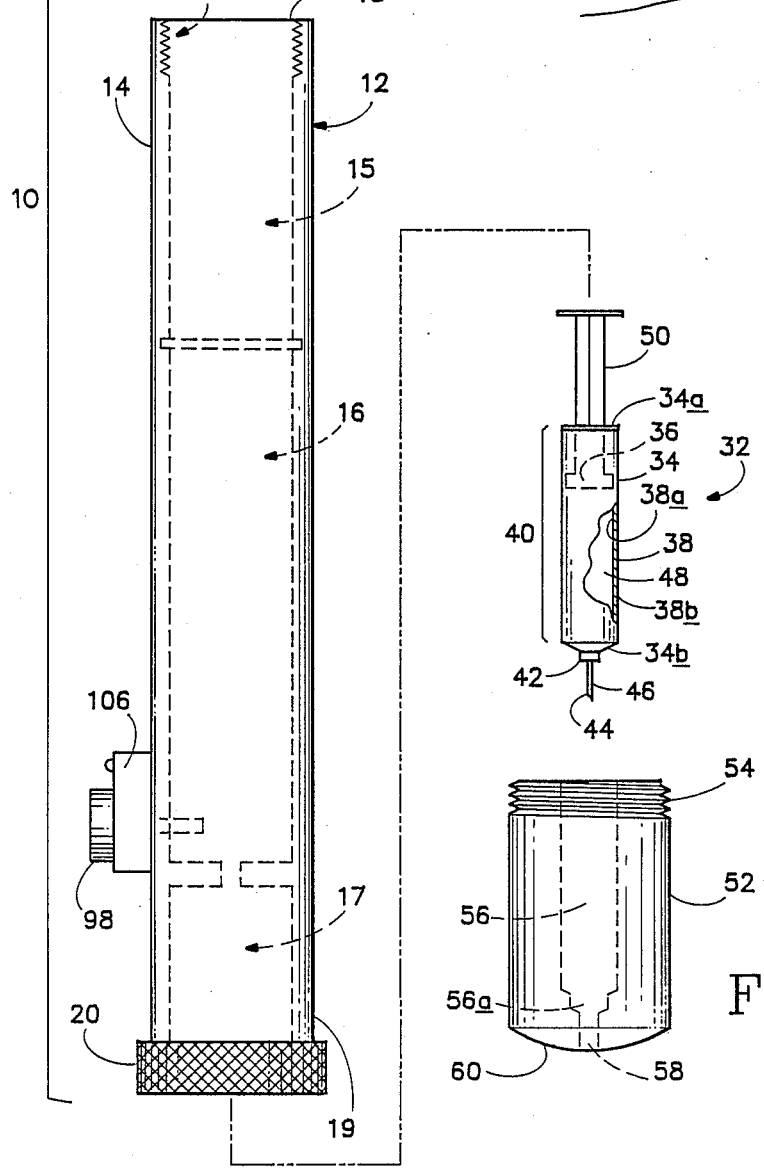
FIG. 4
FIG. 1

NON-INVASIVE HYPODERMIC INJECTION DEVICE

BACKGROUND OF THE INVENTION

The instant invention relates to medication injecting apparatus and specifically to a hypodermic injection device which injects medication but which does not require piercing the skin of a patient with a hypodermic needle.

Known gas powered hypodermic devices generally utilize some form of pressurized gas containing cartridge which includes a frangible seal. The frangible seal must be broken to allow the gas to escape from the cartridge. Known devices provide for release of a gas charge from the cartridge which is immediately used to power a piston, thereby to expel a liquid medication from an ampule. In the event that the seal on the cartridge is not fully or completely broken during the piercing operation, the charge activating a plunger in the ampule may be of insufficient strength to fully expel the contents of the ampule or may be of insufficient strength to expel the contents of the ampule with sufficient force to pierce the skin of the patient.

Known non-invasive hypodermic devices utilize some form of very small orifice or bore which is located at the tip of the ampule through which the medication is expelled. Since the ampules are generally formed of a glass or ceramic material, the process used to form the orifice requires a great deal of position in making an extremely small bore through a crystalline substance. The minimum size of a bore which may be suitably formed in such material is generally larger than that which may be formed in a metallic substance. The formation of orifice in a non-metallic crystalline substance may result in the formation of such an orifice which injects a stream of larger diameter than is possible with a metallic orifice and which in turn creates potential for patient bleeding.

An object of the instant invention is to provide a non-invasive hypodermic device which has a two-stage gas delivery system.

Another object of the instant invention is to provide a non-invasive hypodermic device which has an ampule-enclosing shroud to provide a spaced apart relationship between the patient's skin and orifice means carried on an ampule.

A further object of the instant invention is to provide a non-invasive hypodermic device which may be easily operated with one hand.

Still another object of the instant invention is to provide a non-invasive hypodermic device which has reusable and/or replaceable expendable components.

A further object of the instant invention is to provide a non-invasive hypodermic injection device which includes a refillable ampule.

Another object of the instant invention is to provide an ampule for use in a non-invasive hypodermic device which utilizes a metallic hypodermic needle.

Yet another object of the instant invention is to provide a non-invasive hypodermic device which is simple in construction and is therefore relatively easy and inexpensive to fabricate and assemble and which therefore may be marketed in both reusable and disposable embodiments.

SUMMARY OF THE INVENTION

The instant invention includes a body having a cylindrical sleeve and a hollow interior with open ends and a two-stage gas delivery system therein. The first stage of the system includes a chamber for receiving pressurized means, which in the preferred embodiment takes the form of a cartridge having a gas charge therein. A valve chamber is located adjacent the aforementioned chamber and is in communication therewith. The valve chamber has an exhaust port and includes a valve which is biased to a normally closed position covering the port. The valve chamber is constructed and arranged to contain the gas charge when same is released from the cartridge and the valve is in its normally closed position.

The second stage of the system includes an actuator block, also received in the body, having a passage therethrough. The passage is in communication with the port of the valve chamber. An actuator lever is disposed in the passage. Means for shifting the lever to open the valve are provided. A piston chamber, having a piston therein, is in communication with the passage of the actuator block on one side of the piston.

A medication containing ampule includes a reservoir which is fillable with a supply of medication. The reservoir has a shell which has a wall with inner and outer surfaces. The inner surface has a substantially uniform cross-sectional configuration along a defined length portion of the shell with one end of the shell being open and the other end terminating in a receiving portion having orifice means fixingly received therein. The orifice means has a channel therethrough which is in communication with the reservoir. A plunger is slideably and sealingly disposed within the defined length portion of the shell and is displaceable by the piston between the first position adjacent the open end and a second position adjacent the receiving portion.

An ampule shroud is removably attached to the piston chamber for enclosing the ampule. The shroud includes an opening for receiving therein the orifice means. The shroud and the opening are constructed to maintain a spaced apart relationship between the patient's skin and the orifice means during the course of an injection when the shroud is placed against the patient's skin.

These and other objects and advantages of the instant invention will become more fully apparent as the description which follows is read in conjunction with the drawings.

BRIEF DESCRIPTION OF THE DRAWINGS

FIG. 1 is an exploded side view of the device of the invention.

FIG. 4 is an environmental view of the device in a position ready to administer an injection.

DETAILED DESCRIPTION OF THE PREFERRED EMBODIMENT

Figure 2:
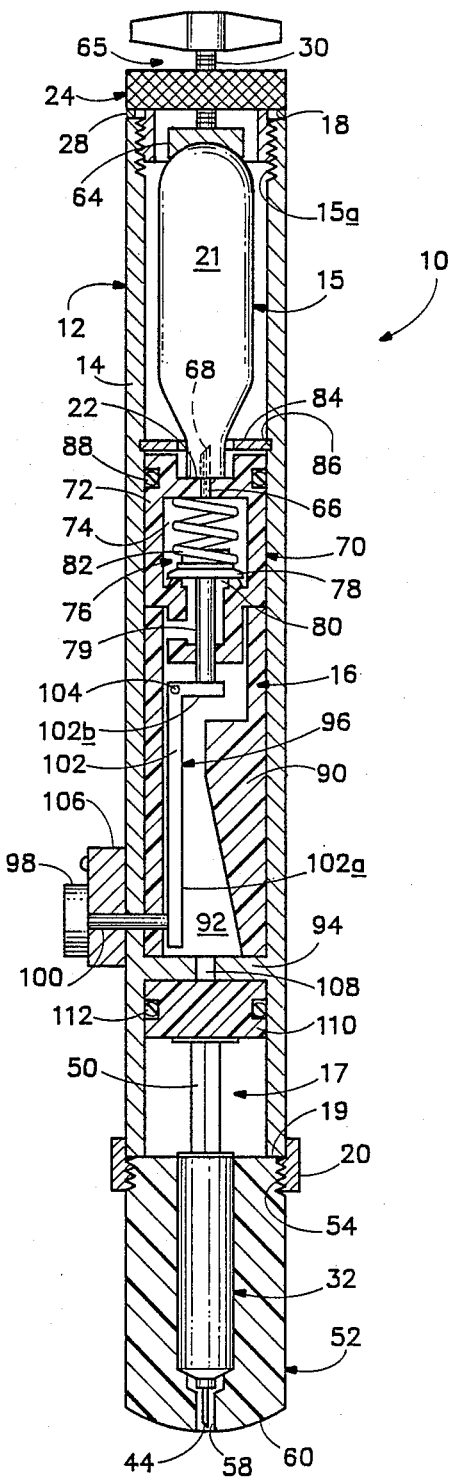
FIG. 2 is a medial section of the invention with the device in a ready condition.

Referring now to the drawings, and initially to FIG. 1, a non-invasive hypodermic injection device constructed according to the invention is shown generally at 10. Device 10 includes a body 12 which includes a generally cylindrical sleeve 14. Sleeve 14 has a hollow interior, which includes a fist chamber 15, having a threaded portion 15a, an actuator-containing portion 16, and a piston chamber 17. Sleeve 14 also includes an open top end 18 and an open bottom end 19. A ring 20 is fixed about bottom end 19. The interior components of sleeve 14 will be described in greater detail later herein.

In the preferred embodiment, a cartridge 21 is used to power device 10. Cartridge 21 includes a frangible seal 22 at an end thereof and contains a gas charge therin.

An end cap 24 is provided to close top end 16. Cap 24 includes a threaded portion 26 which engages conformal threaded portion 15a on the interior of sleeve 14. An O-ring 28 provides a seal between cap 24 and sleeve 14. Cap 14 has a winged-threaded shaft 30 threadably received in the top thereof. Shaft 30 forms part of what is referred to herein as means for releasing the charge in cartridge 21.

An ampule 32 includes a shell 34 and has a plunger 36 received therein. Shell 34 has a wall 38 which has an inner surface 38a and an outer surface 38b. Inner surface 38a has a uniform cross-sectional configuration along a defined length 40 of shell 34. One end 34a of the shell is open for receiving plunger 36. The other end 34b terminates in a receiving portion 42 which has orifice means 44 received therein. In the preferred embodiment, orifice means 44 takes the form of a truncated hypodermic needle. In the preferred embodiment, needle 44 is a 27-guage needle that has a length of approximately 0.375 inches. A channel 46 extends through needle 44 and provides a connection between reservoir 48, formed inside of shell 34, and the outside environment. A supply of medication is received in reservoir 48.

The ampule may be prefilled, or may be refillable with any suitable form of medication.

Plunger, or plunger means, 36 extends above the one end of shell 34 and includes co-action means 50 which co-act with a piston, to be described later herein. Plunger 36 is shiftable between a first position, as shown in FIG. 1, wherein the plunger is extended beyond the one end of shell 34a, and a second position, where the plunger is shifted to a position adjacent receiving portion 42. Shifting plunger between the first and second position, causes the contents of reservoir 48 to be expelled through channel 46 in needle 44.

An ampule shroud 52 has a threaded portion 54 which is received in conformal threads in ring 20 on the bottom end of sleeve 14. Shroud 52 is constructed to completely enclose the portion of ampule 32 which extends beyond sleeve 14. An ampule chamber 56 encloses ampule shell 34. At the lower end of chamber 56 is an opening 58 which is constructed and arranged to maintain a spaced apart relationship between a patient's skin and needle 44. The lower portion of chamber 56 is complimentary to and conformal with receiving portion 42 of ampule 32. An opening 58 is provided at the base of shroud 52. Opening 58 is constructed to be slightly longer than needle 44 in order to provide a clearance of approximately 0.031 inches between the free end of needle 44 and the skin of a patient, which would be juxtaposed with the curved outer end 60 of ampule shroud 52.

Referring now to FIG. 2, the interior construction of body 12 will be further described. As previously mentioned, sleeve 14 includes a first, or cartridge, chamber 15 at the top end thereof. Cartridge, or pressurized means, 21 is received in chamber 15, which is sealed with end cap 24. Shaft 30 extends through cap 24 and terminates in a cartridge contacting element 64. Element 64 is another component of means for releasing the charge in cartridge 21. Shaft 30 and element 64 comprise what is referred to herein as an activator shaft 65.

Another component of means for releasing the charge in cartridge 21 is located at the base of chamber 15. In the preferred embodiment, this takes the form of a puncture pin 66 which has a hollow passage 68 therethrough. Element 64 comprises means for pushing frangible seal 22 over pin 66.

Immediately adjacent chamber 15, in actuator-containing portion 16, is a valve mechanism 70. Mechanism 70 includes a formed portion 72 which defines a valve chamber 74 therein. A valve 76 is located in chamber 74 and includes a valve diaphragm 78 which covers an exhaust port 80 formed in the lower region of formed portion 72. In the preferred embodiment, valve 76 is of the poppet type and is biased to a normally closed position by a spring 82.

Puncture pin 66 is retained in the upper region of formed portion 72 and hollow passage 68 provides communication between the first chamber and the valve, or second, chamber. The cartridge chamber and valve chamber comprise what is referred to herein as the first stage of the two-stage gas delivery system. Valve chamber 74 is constructed and arranged to contain the gas charge of cartridge 20 when the charge is released from the cartridge when frangible seal 22 is broken by puncture pin 66. Formed portion 72 is retained in sleeve 14 by means of a split ring 84 which is received in a groove 86 formed in the interior wall of sleeve 14. A second O-ring 88 is provided to maintain a gas seal about chamber 15 and formed portion 72.

An actuator block 90 is located in portion 16 adjacent formed portion 72. Block 90 includes a passage 92 which extends from port 80 to the base of actuator block 90, where the base contacts a partition 94 formed in sleeve 14. Block 90 also contains actuator means, shown generally at 96, for opening valve 76. Actuator means 96 includes an actuator button 98 which is mounted on the side of sleeve 14 and is connected to an actuator button shaft 100 which extends through the side sleeve 14. Block 90 forms a partially gas-tight seal about shaft 100. The free end of shaft 100 contacts an L-shaped actuator lever 102 which has a long leg 102a and a short leg 102b. Lever 102 is pivoted about a pin 104, located near the apex of lever 102.

In the preferred embodiment, leg 102a has a functional length approximately 8 times that of leg 102b. Functional length, in this context, is the distance between the point of contact of leg 102a and leg 102b with shaft 100 and shaft 79, respectively, and the rotational point, defined by pin 104. This provides a mechanical advantage of approximately 8:1 for opening poppet valve 76. Under normal operating conditions, a force of approximately 40 pounds is required to open valve 76. The mechanical advantage gained by the use of lever 102 requires a force of approximately 5 pounds, applied to button 98, to operate the device.

A safety lock 106 prevents inadvertent depression of button 98. When lock 106 is swung away from button 98, as depicted in FIG. 3, button 98 and shaft 100 may be depressed, thereby pivoting lever 102 about pin 104, which in turn pushes on valve shaft 79, thereby opening port 80, allowing the gas contained in valve chamber 74 to enter passage 96.

Returning now to FIG. 2, partition 94 has a bore 108 therethrough which connects passage 96 with piston chamber 17. Chamber 17 contains a moveable piston 110 therein, and has an O-ring 112 thereabout to form a seal with the walls of chamber 17.

Device 10 is shown in a ready condition in FIG. 2. Cartridge 21 has been forced down over puncture pin 66 and the charge contained in cartridge 21 has been released, filling chambers 15 and 74. Plunger 110 is at the upper most region of chamber 17, in contact with co-action means 50. A supply of medication in reservoir 48 is ready to be injected into a patient.

Figure 3:
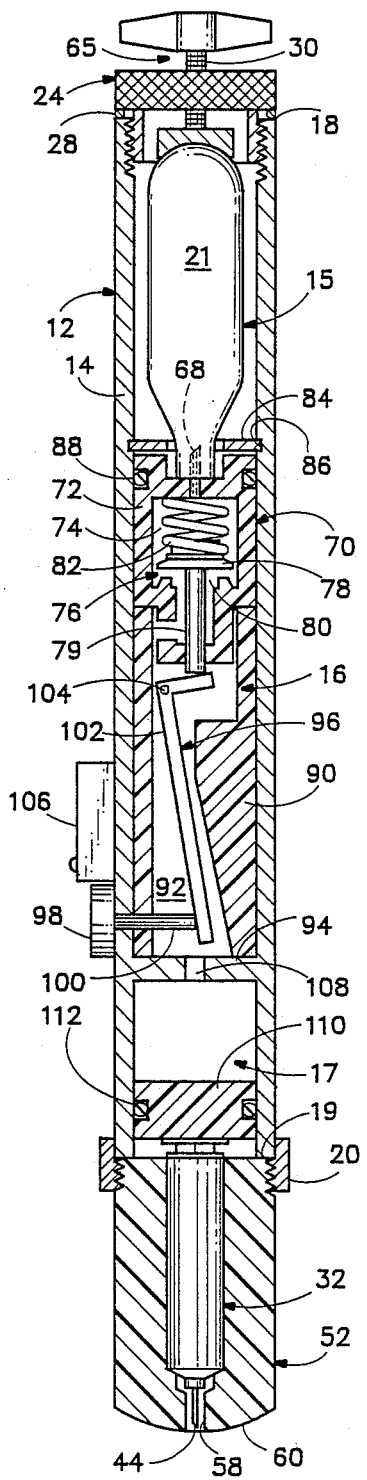
FIG. 3 is a medial sectional view of the device in a discharged condition.

Turning now to FIG. 3, the device is shown in a discharged condition. Safety lock 106 has been swung free of actuator button 98 allowing button 98 to be depressed thereby shifting actuator lever 102 against valve shaft 79. Button 98 and shaft 100 have a travel of about between 0.25 and 0.33 inches in the preferred embodiment, which is sufficient to displace shaft 98 and diaphragm 78 a sufficient distance to fully open valve 76. The construction of valve 76 provides a complete, immediate release of the gas contained in chamber 74 into passage 92, through bore 108 and against the upper surface of piston 110. This results in the rapid displacement of piston 110 against co-action means 50, thereby discharging the contents of reservoir 48.

Operation

The ampule, or syringe, may be provided prefilled or may be filled with desired medication. The ampule may be used to inject various amounts of medication, generally up to 3 cc. The filled ampule is placed in the shroud and properly seated.

Piston 110 is moved to a position adjacent partition 94. This may be accomplished by means of a push rod, pencil, etc. Shroud 52, containing ampule 32, is now mated to sleeve 14 by inserting co-action means 50 into the free space of piston chamber 17 and securing shroud 52 to sleeve 14 by means of ring 20. Safety lock 106 is positioned to prevent displacement of button 98.

Cartridge 21 is then inserted into chamber 15 such that frangible seal 22 contacts, but is not pierced by, puncture pin 66. Threaded shaft 30 has previously been withdrawn as far as it will go, thereby displacing element 64 to the upper most portion of cap 24. Cap 24 is then secured to sleeve 14 where it it sealed by O-ring 28. Activator shaft 65 is then rotated such that element 64 contacts the top of cartridge 21 and presses frangible seal 22 over pin 66, thereby breaking the seal and discharging the charge in cylinder 21 into valve chamber 74. The device is now in the condition shown in FIG. 2 and is ready for use.

Referring now to FIG. 4, device 10 is brought adjacent an injection site 116, which is depicted on a patient's arm 118. Safety lock 106 is released and the device held generally perpendicular to the injection site. Button 98 is then depressed, causing lever 102 to shift, displacing shaft 98 and opening valve 76. The gas charge is instantly released from chamber 74 through passage 92 and bore 108, thereby displacing piston 110. This in turn causes co-action means 50 and plunger 36 to move rapidly toward the receiving portion of ampule 32, injecting the contents of reservoir 48.

A venting system is provided in chamber 17 to release the unused gas once piston 110 has traveled its full distance. When button 98 is released, the charge remaining in passage 92 will exhaust around shaft 100.

To remove the used contents of the device, activator shaft 65 is initially unscrewed, which will permit the unused gas to escape from chambers 15 and 74. End cap 24 is next removed and the cartridge discarded. Shroud 52 is next removed and ampule 32 either discarded or prepared for its next use.

Ampule 32 is designed much like a conventional syringe which allows the ampule to be refilled with medication from a conventional dispensing vile which has a puncturable seal over the top thereof.

Alternatively, the ampules may come pre-loaded with medication, in which case they would be provided in a sterile, sealed package. In either case, there is very little leakage of medication through needle 44 because of its very small diameter, which, for a 27-gauge needle is generally 0.008 inches.

The cartridges used with the device of the invention in the preferred embodiment are filled with $CO_2$ and are generally charged to between 700–800 pounds per square inch. This charge results in fluid pressures through needle 44 of between 5000 and 6000 pounds per square inch, which is sufficient to pierce the skin with a fluid stream only, thereby providing a subcutaneous injection without contaminating needle 44 on ampule 32. By slightly changing the gauge of needle 44, and/or increasing the effective pressure, a fluid stream may be generated having sufficient pressure to administer intramuscular injection. Non-invasive injection generally precludes any bleeding from the injection site, although in some instances a drop or two of blood may be expelled from the injection site.

Thus a non-invasive hypodermic injection device has been disclosed. The device utilizes a two-stage gas delivery system to ensure that a charge contained in a gas cartridge is fully released into the device prior to use. An ampule containing shroud receives an ampule having a truncated hypodermic needle at one end thereof and maintains spacing between the end of the needle and the skin of a patient being injected.

Although a preferred embodiment of the device has been disclosed, it should be appreciated that variations and modifications may be made thereto without departing from the spirit and scope of the invention.

It is claimed and desired to secure as Letter Patent:

1. A non-invasive hypodermic injection device, means having a gas charge therein, for injecting a medication through a patient's skin, comprising:
  a body including:
  a first chamber containing the charge;
  a valve chamber having an exhaust port and a normally closed valve closing said port, said valve chamber being constructed and arranged to contain the gas charge when same is released from the first chamber and said valve is in its normally closed condition;
  a piston chamber operably connected to said port and having a moveable piston therein; and
  actuator means for opening said valve, said valve, when open, allowing gas to flow from said valve chamber, through said port, to said piston chamber thereby displacing said piston;
  a medication containing ampule including a reservoir for retaining a supply of medication, orifice means located on and extending beyond one end of said reservoir, said orifice means having a passage therein for allowing transit of the medication therethrough, and plunger means, received in siad reservoir, moveable from adjacent the other end of said reservoir towards said orifice means, and including co-action means for moving said plunger with said piston; and an ampule shroud having an ampule chamber therein for receiving said ampule, said ampule shroud enclosing said ampule, said shroud defining an opening for receiving therein said orifice means, said shroud and said opening being constructed and arranged to maintain a spaced apart relationship between the patient's skin and said orifice means during the course of an injection when said shroud is placed against the patient's skin.

2. The device of claim 1 wherein said orifice means includes a truncated hypodermic needle fixed to said reservoir and said passage extends through said needle into said reservoir.

3. The device of claim 1 wherein said first chamber has an open top sized to receive a gas-charge containing cartridge having a frangible seal thereon; and wherein said means for releasing the charge includes a puncture pin at the base of the chamber, said puncture pin being constructed and arranged to puncture the frangible seal of the cartridge, and an end cap sealably received in said open top, said cap including means for pushing the frangible seal over said puncture pin.

4. The device of claim 3 wherein said valve chamber is disposed adjacent said first chamber and wherein said puncture pin includes a hollow passage communicating between said first chamber and said valve chamber.

5. The device of claim 1 wherein said valve is of the poppet type, including a valve diaphragm disposed over said port in said valve chamber, a spring biasing said diaphragm to its normally closed position, a valve shaft affixed to said diaphragm and extending through said port, said shaft being operable with said actuator means to open said valve.

6. The device of claim 5 wherein said actuator means includes an actuator button disposed on the outside of the body, an actuator button shaft extending through the body sidewall and an actuator lever, said lever having a generally L-shaped configuration with the long leg of the L contacting said button shaft and the short leg of the L contacting said valve shaft, said lever being pivotably mounted adjacent the apex of the two legs, said lever being operable, when said button is depressed towards said body, to shift said valve shaft axially thereby opening said valve.

7. The device of claim 6 wherein said long leg has a functional length substantially 8 times as long as that of said short leg, thereby providing a mechanical advantage of 8:1 for opening said valve.

8. A non-invasive hypodermic injection device, in combination with a pressurized cartridge having a gas charge therein and including a frangible seal, for injecting a medication through a patient's skin, comprising:
 a body having a cylindrical sleeve and a hollow interior with open ends and a two-stage gas delivery system therein, the first stage of said system including:
 a cartridge chamber for receiving the cartridge, including means for releasing the charge contained in the cartridge and;
 a valve chamber located adjacent said cartridge chamber in communication therewith, having an exhaust port and including a poppet valve which is biased to a normally closed position covering said port, said chamber being constructed and arranged to contain the gas charge when same is released from said cartridge and said valve is in its normally closed position; and
 the second stage of the system including:

an actuator block having a passage therethrough, said passage communicating with said port in said valve chamber;
 an actuator lever disposed in said passage; and
 means for shifting said lever thereby to open said valve and;
 a piston chamber having a piston therein, said chamber communicating with said passage on one side of said piston and;
 a medication containing ampule including a reservoir, said reservoir being fillable with a supply of medication, having a shell which has a wall with inner and outer surfaces, said inner surface being characterized by a substantially uniform cross sectional configuration along a defined length portion of said shell, one end of said shell being open and the other end terminating in a receiving portion having orifice means fixedly received therein, said orifice means having a channel therethrough, said channel communicating with said reservoir, and a plunger slideably and sealingly disposed within said defined length portion in said shell, displaceable by said piston between a first position adjacent said open end and a second position adjacent said receiving portion; and
 an ampule shroud removably attached to said piston chamber for enclosing said ampule, said shroud including an opening in one end thereof for receiving therein said orifice means, said shroud and said opening being constructed and arranged to maintain a spaced apart relationship between the patient's skin and said orifice means during the course of an injection when said one end of said shroud is placed against the patient's skin.

9. The device of claim 8 wherein said orifice means includes a truncated hypodermic needle fixed to said reservoir and said channel extends through said needle into said reservoir.

10. The device of claim 8 wherein said cartridge chamber has an open top sized to receive the cartridge; and wherein said means for releasing the charge includes a puncture pin at the base of the chamber, said puncture pin being constructed and arranged to puncture the frangible seal of the cartridge, and an end cap sealably received in said open top, said cap including means for pushing the frangible seal over said puncture pin.

11. The device of claim 8 wherein said poppet valve includes a valve diaphragm disposed over said port in said valve chamber, a spring biasing said diaphragm to its normally closed position, and a valve shaft affixed to said diaphragm and extending through said port, said shaft being operable with said actuator lever to open said valve.

12. The device of claim 11 wherein said means for shifting said actuator lever includes an actuator button disposed on the outside of the body, and an actuator button shaft extending through the body sidewall, and said actuator lever has a generally L-shaped configuration with the long leg of the L contacting said button shaft and the short leg of the L contacting said valve shaft, said lever being pivotably mounted adjacent the apex of the two legs, said lever being operable, when said button is depressed towards said body, to shift said valve shaft axially thereby opening said valve.

13. A non-invasive hypodermic injection device, means having a gas charge therein, for injecting a medication through a patient's skin, comprising:

a body including:

a first chamber containing the gas charge including means for releasing the charge;

a piston chamber selectively, operably connected to said first chamber, and having a movable piston therein;

a medication containing ampule including a reservoir for retaining a supply of medication, orifice means located on one end of said reservoir, said orifice means having a passage therethrough for allowing dispensing of the medication, and plunger means received in said reservoir, moveable from adjacent the other end of said reservoir towards said orifice means, and including co-action means for moving said plunger with said piston; and an ampule shroud having an ampule chamber therein for receiving said ampule, said shroud defining an opening for receiving therein said orifice means, said shroud and said opening being constructed and arranged to maintain a spaced apart relationship between the patient's skin and said orifice means during the course of an injection when said shroud is placed against the patient's skin.

14. The device of claim 13 wherein said orifice means includes a truncated hypodermic needle fixed to said reservoir and said passage extends through said needle into said reservoir.

15. The device of claim 13 which further includes a valve chamber having an exhaust port and a normally closed valve closing said port, said valve chamber being constructed and arranged to communicate with said first chamber and to contain the gas charge when same is released and said valve is in its normally closed condition.

16. The device of claim 15 which further includes actuator means for opening said valve, said valve, when open, allowing gas to flow from said valve chamber, through said port, ot said piston chamber thereby displacing said piston.

17. The device of claim 16 wherein said first chamber has an open top sized to receive a gas-charge containing cartridge therein, said cartridge having a frangible seal at one end thereof; and wherein said means for releasing the charge includes a puncture pin at the base of the chamber, said puncture pin being constructed and arranged to puncture the frangible seal of the cartridge; and an end cap sealably received in said open top, said cap including means for selectively pushing the frangible seal over said puncture pin.

18. The device of claim 17 wherein said valve chamber is disposed adjacent said first chamber and wherein said puncture pin includes a hollow passage communicating between said first chamber and said valve chamber.

19. The device of claim 15 wherein said valve is of the poppet type, including a valve diaphragm disposed over said port in said valve chamber, a spring biasing said diaphragm to its normally closed position, a valve shaft affixed to said diaphragm and extending through said port, said shaft being operable with said actuator means to open said valve.

20. The device of claim 19 wherein said actuator means includes an actuator button disposed on the outside of the body, an actuator button shaft extending through the body sidewall and an actuator lever, said lever having a generally L-shaped configuration with the long leg of the L contacting said shaft and the short leg of the L contacting said valve shaft, said lever being pivotably mounted adjacent the apex of the two legs, said lever being operable, when said button is depressed towards said body, to shift said valve shaft axially thereby opening said valve.

21. A non-invasive hypodermic injection device, in combination with a pressurized cartridge having a gas charge therein and including a frangible seal, comprising:

a body having a cylindrical sleeve and a hollow interior with open ends and a two-stage gas delivery system therein;

the first stage of said system including:

a cartridge chamber for receiving the cartridge, said cartridge chamber having an open top sized to receive the cartridge and including a puncture pin at the base of the chamber, said puncture pin being constructed and arranged to puncture the frangible seal of the cartridge, and an end cap sealably received in said open top, said cap including an activator shaft threadably received in said cap constructed and arranged to co-act with the cartridge thereby to push the frangible seal onto said puncture pin when said activator shaft is screwed into said cap thereby to release the charge contained in the cartridge; and a valve chamber located ajacent said cartridge chamber in communication therewith; having an exhaust port and including a poppet valve which is biased to a normally closed position covering said port, said chamber being constructed and arranged to contain the gas charge when same is released from said cartridge and said valve is in its normally closed position; and the second stage of the system including;

an actuator block having a passage therethrough, said passage communicating with said port in said valve chamber;

an actuator lever disposed in said passage; and means for shifting said lever thereby to open said valve; and a piston chamber having a piston therein, said chamber communicating with said passage on one side of said piston; and a medication-containing ampule including a reservoir, said reservoir being fillable with a supply of medication, having a shell which has a wall with inner and outer surfaces, said inner surface being characterized by a substantially uniform cross sectional configuration along a defined length portion of said shell, one end of said shell being open and the other end terminating in a receiving portion having a truncated hypodermic needle fixed thereto, said needle having a channel therethrough, said channel communicating with said reservoir, and a plunger slideably and sealingly disposed within said within said defined length portion in said shell, displaceable by said piston between a first position adjacent said open end and a second position adjacent said receiving portion; and an ampule shroud removably attached to said piston chamber for enclosing, completely, said ampule, said shroud including an opening for receiving therein said needle, said shroud and said opening being costructed and arranged to maintain a spaced apart relationship between the patient's skin and said needle means during the course of an injection when said shroud is placed against the patient's skin.

22. The device of claim 21 wherein said poppet valve includes a valve diaphragm disposed over said port in said valve chamber, a spring biasing said diaphragm to its normally closed position, a valve shaft affixed to said diaphragm and extending through said port, said shaft being operable with said actuator lever to open said valve.

23. The device of claim 22 wherein said means for shifting said actuator lever includes an actuator button disposed on the outside of the boyd, and an actuator button shaft extending through the body sidewall, and said actuator lever has a generally L-shaped configuration with the long leg of the L contacting said button shaft and the short leg of the L contacting said valve shaft, said lever being pivotably mounted adjacent the apex of the two legs, said lever being operable, when said button is depressed towards said body, to shift said valve shaft axially thereby opening said valve.

24. The device of claim 21 which further includes a supply of medication contained in said ampule.

* * * * *